United States Patent
Mennen et al.

(10) Patent No.: US 9,732,033 B2
(45) Date of Patent: Aug. 15, 2017

(54) UREA PRODUCTION PLANT

(71) Applicant: Stamicarbon B.V., Sittard (NL)

(72) Inventors: Johannes Henricus Mennen, Sittard (NL); Jozef Hubert Meessen, Sittard (NL)

(73) Assignee: Stamicarbon B.V., Sittard (NL)

( * ) Notice: Subject to any disclaimer, the term of this patent is extended or adjusted under 35 U.S.C. 154(b) by 0 days.

(21) Appl. No.: 15/246,334

(22) Filed: Aug. 24, 2016

(65) Prior Publication Data

US 2016/0362360 A1    Dec. 15, 2016

Related U.S. Application Data

(62) Division of application No. 14/398,433, filed as application No. PCT/NL2013/050328 on May 2, 2013, now Pat. No. 9,458,098.

(30) Foreign Application Priority Data

May 3, 2012    (EP) .................................. 12166575

(51) Int. Cl.
| | | |
|---|---|---|
| C07C 273/04 | (2006.01) | |
| B01D 5/00 | (2006.01) | |
| B01D 47/00 | (2006.01) | |
| B23P 15/26 | (2006.01) | |
| B01J 10/00 | (2006.01) | |

(52) U.S. Cl.
CPC ............ *C07C 273/04* (2013.01); *B01D 5/006* (2013.01); *B01D 5/009* (2013.01); *B01D 47/00* (2013.01); *B01J 10/00* (2013.01); *B23P 15/26* (2013.01); *Y10T 29/49352* (2015.01)

(58) Field of Classification Search
CPC ...... C07C 273/04; B01D 47/00; B01D 5/006; B01D 5/009; B23P 15/26
See application file for complete search history.

(56) References Cited

U.S. PATENT DOCUMENTS

| | | | |
|---|---|---|---|
| 4,613,697 A | 9/1986 | Pagani | |
| 5,176,800 A * | 1/1993 | Zardi | C07C 273/04 |
| | | | 159/47.2 |
| 5,812,539 A | 9/1998 | Dent et al. | |
| 6,342,632 B1 * | 1/2002 | Pagani | C07C 273/04 |
| | | | 564/67 |
| 2007/0287863 A1 | 12/2007 | Komiti | |
| 2010/0210874 A1 * | 8/2010 | Zardi | B01F 5/0451 |
| | | | 564/67 |
| 2011/0229394 A1 | 9/2011 | Niehues et al. | |

FOREIGN PATENT DOCUMENTS

| | | |
|---|---|---|
| CN | 1100412 | 9/1995 |
| EP | 1 525 187 | 1/2009 |
| JP | 50-142515 | 11/1975 |
| JP | 56-110663 | 9/1981 |
| JP | 2000-001466 | 1/2000 |
| JP | 2008-505888 | 2/2008 |
| JP | 2013-503913 | 2/2013 |
| WO | WO-96/23767 | 8/1996 |
| WO | WO-03/087043 | 10/2003 |
| WO | WO-2006/004395 | 1/2006 |
| WO | WO-2006/004424 | 1/2006 |
| WO | WO-2009/043365 | 4/2009 |
| WO | WO-2011/029625 | 3/2011 |
| WO | WO-2011/032786 | 3/2011 |

OTHER PUBLICATIONS

Black, "Engineering in Plant Revamp Work," Industrial and Engineering Chemistry (1954) p. 2471.
Elvers et al., "Ullmann's Encyclopedia of Industrial Chemistry," VCH Verlagsgesellschaft (1996) 5(27):333-365.
International Search Report for PCT/NL2013/050328, mailed Jun. 13, 2013, 4 pages.
Nitrogen "Revamping urea plants," (1985) 157:37.
Nitrogen+Syngas, "Innovative ammonia emission reductions," (2008) pp. 38-41.
Potthoff, "Jumbo single-line urea granulation plants—Ready for Implementation," (2011) Roermond, The Netherlands pp. 213-218.
ThyssenKrupp Industrial Solutions, "UFT fluid bed granulation Superior technology," (2006) pp. 1-16.
ThyssenKrupp Industrial Solutions, "Urea" (2007) pp. 1-24.
Franzrahe, "Meeting environmental issues facing new and existing urea fluid-bed granulation plants," 24th AFA International Technical Fertilizer Conference (2011) pp. 1-18.
Nishikawa, "Toyo's Approach to Environmental Protection in Urea Plants," Nitrogen+Syngas 2011 International Conference (2011) pp. 157-163.
Sobhi and Roos, "Experience at Alexfert'S World-Scale Stamicarbon Fluidized-Bed Urea Granulation Plant," Nitrogen+Syngas International Conference and Exhibition (2007) pp. 2-10.

* cited by examiner

*Primary Examiner* — Sudhakar Katakam
(74) *Attorney, Agent, or Firm* — Morrison & Foerster LLP

(57) ABSTRACT

Disclosed is a plant for the production of urea. The plant comprises conventional sections for synthesis and recovery, for evaporation and condensation, for urea finishing, and for dust scrubbing. According to the invention, an additional evaporation and condensation loop is introduced from and to the dust scrubbing section. This loop results in a more favorable energy consumption of the plant.

5 Claims, 2 Drawing Sheets

UREA PRODUCTION PLANT

CROSS-REFERENCE TO RELATED APPLICATION

This application is a divisional of U.S. Ser. No. 14/398,433 now U.S. Pat. No. 9,458,098 having an international filing date of 2 May 2013, which is the national phase of PCT application PCT/NL2013/050328 having an international filing date of 2 May 2013, which claims benefit of European patent application No. 12166575.6 filed 3 May 2012. The contents of the above patent applications are incorporated by reference herein in their entirety.

FIELD OF THE INVENTION

The invention is in the field of urea production, and particularly pertains to the production of solid urea particles (urea finishing). The invention particularly pertains to reducing the energy consumption in such a process. The invention also pertains to a urea production plant, and to revamping an existing urea production plant.

BACKGROUND OF THE INVENTION

Urea is generally produced from ammonia and carbon dioxide. It can be prepared by introducing an ammonia excess together with carbon dioxide at a pressure between 12 and 40 MPa and at a temperature between 150° C. and 250° C. into a urea synthesis zone. The resulting urea formation can be presented best in the form of two consecutive reaction steps, in the first step ammonium carbamate being formed according to the exothermic reaction:

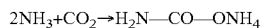

after which the ammonium carbamate formed is dehydrated in the second step to give urea according to the endothermic equilibrium reaction:

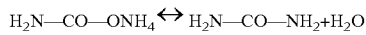

The extent to which these reactions take place depends among other things on the temperature and the ammonia excess used. The reaction product obtained in a urea synthesis solution substantially consists of urea, water, unbound ammonia and ammonium carbamate. The ammonium carbamate and the ammonia are removed from the solution and are generally returned to the urea synthesis zone.

In addition to the above-mentioned solution in the urea synthesis zone, a gas mixture is formed which consists of unconverted ammonia and carbon dioxide together with inert gases, the so called reactor off-gas. The urea synthesis section may comprise separate zones for the formation of ammonium carbamate and urea. These zones may also be combined in a single apparatus.

The background of this invention is a urea production plant comprising the following sections: (A) a synthesis and recirculation (recovery) section; said section being in fluid communication with an evaporation section (B), said evaporation section being in fluid communication with a finishing section (C); said finishing section (C) having a gas flow line to a dust scrubbing section (D); and wherein the evaporation section (B) further comprises a gas flow line to a condensation section (E). Said condensation section (E) being in fluid communication with a process condensate treatment section (F). A conventional set-up is shown in FIG. 1.

From the synthesis and recovery section (A), a solution (3) results, consisting mainly of urea and water, however contaminated with small residual amounts of ammonium carbamate and a small residue of excess ammonia. A typical composition of this solution (3) is 60-85% (wt) Urea, 0.1-2.5% (wt) of ammoniumcarbamate, 0.1-2.5% (wt) of ammonia.

In the evaporation section (B), said solution (3) is separated into a (liquid) concentrated urea melt (4) and a gaseous stream (11). Typically, the urea melt in this section is concentrated to a final moisture content of 0.2-5.0% by weight. The evaporation section is operated under vacuum conditions. It may comprise one or more evaporators in series. The small amount of residual ammonium carbamate present in the evaporation feedstream (3) will decompose into $NH_3$ and $CO_2$ in these evaporators. Under these vacuum conditions, this $NH_3$ and $CO_2$ subsequently mainly is transferred into the gaseous stream (11). Also the small amount of excess ammonia, present in the evaporation feedstream (3) is evaporated under this vacuum conditions and transferred to gas stream (11).

The finishing section (C) may be a prilling tower, or a granulation section. The granulation section may be a fluidized bed-granulation, or a drum granulation, or a pan-granulation, or any other similar and known granulation device. The main function of this finishing section is to transfer the urea melt (4) into a stream of solidified particles (5). These solidified particles, usually called 'prills' or 'granules' is the main product stream from the urea plant. In any event, to transfer the urea from the liquid phase into the solid phase, the heat of crystallization has to be removed. Moreover, usually some additional heat is removed from the solidified urea particles, in order to cool them to a temperature that is suitable for safe and comfortable storage and transport of this final product. The resulting total removal of heat in the finishing section is usually done in two ways: (i) by evaporation of water. This water enters the finishing section either as part of the urea melt, or is sprayed as liquid water at an appropriate place in the finishing process; (ii) by cooling with air. Usually most of the crystallization/cooling heat is removed by cooling with air. The cooling air is supplied to the finishing section via (6); by the nature of cooling air, it is heated up and leaves the finishing section via (7). Usually an amount of air equal to 3-30 kg of air per kg of final solidified product is applied.

In the finishing section (C), the air comes into direct contact with the urea melt and with the solidified urea particles. This inadvertently leads to some contamination of the air with some urea dust. Depending on the nature of the finishing section (prilling/granulation, type of granulation, conditions selected in granulation), the amount of dust present in the air may vary widely, values in the range of 0.05% to 10% (with respect to the final product flow) have been observed. This presence of dust in the air stream (7) usually makes a dust removal system (D) required, either for environmental or from economical considerations, before the air can be vented back into the atmosphere.

In the dust scrubbing section (D), dust scrubbing is usually done using a circulating urea solution as washing agent. On top of this also fresh water scrubbing usually is applied. The air entering via (7), by its nature of cooling air in finishing section (C), is hot. Therefore a considerable amount of water will evaporate in the dust scrubbing section D. This loss of water is made up by supply of fresh water via (10). The water used for this purpose (10) should be free of any volatile components (such as for instance $NH_3$ and $CO_2$), since any volatile components in the dust scrubbing section D would be transferred into the air, and thus result in contamination of the airflow (8) that is returned into the atmosphere. Such a contamination would be undesirable from an environmental point of view.

In the dust scrubbing section D a purge flow of urea solution (9) is obtained. This purge flow (9) usually has a concentration of 10-60% (by wt) of urea. In order to reprocess the urea present in this purge flow, the purge flow (9) is returned to the evaporation section (B), where it is further concentrated and then recycled to the finishing section (C). Cleaned air is vented from the dust scrubbing via (8) into the atmosphere.

The vapour stream (11) originating from the evaporation section (B), which is normally contaminated with low amounts of $NH_3$ and $CO_2$, is sent to a condensation section (E). Depending on the set up of the evaporation section this may be in the form of a single gas stream, or as multiple gas streams. In any case, the gas stream(s) 11 is/are condensed in section E using known vacuum condensation techniques, usually a combination of cooling water cooled shell and tube heat exchangers and steam driven vacuum ejectors. For these vacuum ejectors steam is required (stream S1). The condensed gas streams are removed as an aqueous solution (12) from the condensation section.

The aqueous solution (12) is lead to a process condensate treatment section (F). The aqueous solution (12) from the condensation section contains mainly water, however this water is contaminated with the $NH_3$ and $CO_2$ originating from gas stream (11). Also, in practice, the aqueous solution (12) contains some urea, as a result of entrainment of urea into the gas phase in evaporation section (B). Because of the presence of these contaminants, the water has to be treated for environmental and/or for economical reasons before the water can be purged from the process. Usually such a process condensate treatment section F contains a deep hydrolysis section, where any urea present is converted into $NH_3$ and $CO_2$ and a steam stripping section to remove $NH_3$ and $CO_2$ from the water. Both the deep hydrolysis, as well as the steam stripping operation requires valuable steam. This steam is indicated by (S2) in FIG. 1. In the art, there is a continuous desire to minimize the amount of steam required for this purpose. Also, there is a continuous desire to minimize the amount of water to be treated in this section (F), since a lower amount of water to be treated will minimize the dimensions of the equipment items required in this section, and thus minimize the required investment cost for this process condensate treatment section.

The $NH_3$ and $CO_2$ removed from the waste water is recycled to section A via line (13). This recycle stream (13) can be either in liquid or gas, but in any case usually contains some water too. The cleaned water leaves the process condensate treatment section via (14). This cleaned water may be a very good source of water to be applied in dust scrubbing section (D). In this case the amount of water produced in section (F) usually is more than the amount of water required in section (D), such that some purge flow (15) of purified water remains.

SUMMARY OF THE INVENTION

In order to better address one or more of the foregoing desires, the invention, in one aspect, provides a urea production plant comprising a synthesis and recovery section (A); said section being in fluid communication with an evaporation section (B), said evaporation section being in fluid communication with a finishing section (C) and having a gas flow line to a condensation section (E); said finishing section (C) having a gas flow line to a dust scrubbing section (D); wherein the plant comprises an additional evaporation section (G) placed downstream of the dust scrubbing section (D), and wherein said additional evaporation section (G) is in fluid communication with the finishing section (C); wherein the additional evaporation section (G) has a gas flow line to an additional condensation section (H), and wherein the additional condensation section (H) is in fluid communication with the dust scrubbing section (D).

The invention, in another aspect, presents a method of modifying an existing urea plant of the foregoing type, by adding to the plant an additional evaporation section (G) placed downstream of the dust scrubbing section (D), said additional evaporation section (G) being placed such as to be in fluid communication with the finishing section (C); wherein the additional evaporation section (G) has a gas flow line to an additional condensation section (H), and wherein the additional condensation section (H) is in fluid communication with the dust scrubbing section (D).

In yet another aspect, the invention provides a process for the preparation of urea comprising the steps of (a) one or more synthesis and recovery steps wherein ammonia and carbon dioxide are reacted to form urea and wherein an aqueous solution comprising urea is formed; (b) an evaporation step wherein water is evaporated from the aqueous solution formed in (a) so as to result in a concentrated urea-comprising liquid and an aqueous vapour phase; (c) subjecting the concentrated urea-comprising liquid to a finishing treatment resulting in solid urea, wherein heat is removed by means of a cooling gas such as air; (d) subjecting the cooling gas to dust scrubbing, wherein urea is recovered in an aqueous stream; (e) subjecting said aqueous stream to evaporation so as to result in an additional concentrated urea-comprising liquid and a vapour stream, wherein the evaporation is conducted in an evaporation step separate from the evaporation step (b), wherein the additional concentrated urea-comprising liquid is further subjected to the finishing step (c), and wherein vapours originating from the separate evaporation step are subjected to a separate condensation step (f), and wherein the condensate from said separate condensations step (f) is used in the dust scrubbing step (d).

DETAILED DESCRIPTION OF THE INVENTION

Figure 1:
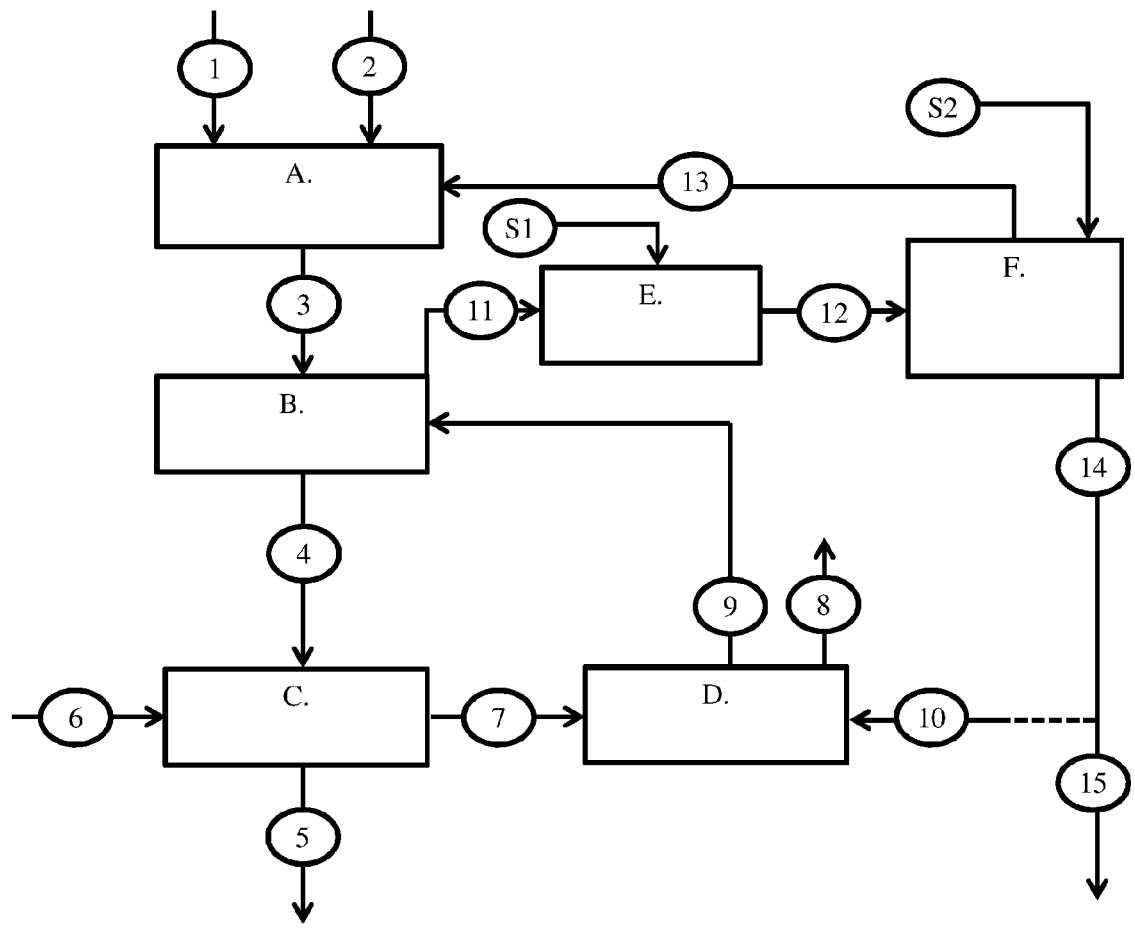
FIG. 1 is a schematic representation of a conventional urea production plant.

In a general sense, the invention is based on the judicious insight to include an additional evaporation loop in the process. The additional evaporation loop, as defined, surprisingly reduces the energy consumption downstream of the condensation section (E). Typically, downstream of the condensation section (E) one will find a process condensate treatment section (F).

The additional evaporation loop is provided for by adding a second evaporation section (G) and a second condensation section (H) to the plant. Particularly, the liquids obtained in the second condensation section are used in the dust scrubbing section (D).

Where, in this description, it is spoken of "fluid communication", this refers to any connection between a first part or section of a plant and a second part or section of a plant via which fluids, notably liquids, can flow from the first part of the plant to the second part of the plant. Such fluid communication is typically provided by piping systems, hoses, or other devices well-known to the skilled person for the transportation of fluids.

Where in this description it is spoken of "gas flow lines" this refers to any connection between a first part or section of a plant and a second part or section of a plant via which gas or vapours, notably aqueous vapours, can flow from the first part of the plant to the second part of the plant. Such gas flow lines typically comprise piping systems, or other devices well-known to the skilled person for the transportation of gases, if needed under above or below (vacuum) atmospheric pressures.

The invention is applicable both to the construction of new urea plants ("grass root" plants) as well as in revamping existing urea plants.

In case of a newly constructed urea plant, the required investment for the process condensate treatment section (F) is considerably reduced by the measures of the invention, viz. to build-in an additional evaporation section (G) and an additional evaporation section (H) in such a way as to create an evaporation and condensation loop from and to the dust scrubbing section.

The second evaporation section (G) is fed with the urea solution (9) purged from the dust scrubbing section (D). This second evaporation section, just as the main evaporation section B, may comprise one or more evaporators. Therein the urea solution (9) is concentrated, generally under vacuum, to a concentration that allows feeding the concentrated solution (16) as a co-feed to the finishing section C. The off-gas or off-gasses (17) from the second evaporation section are condensed in a second condensation section (H). Like the first condensation section (E), this second condensation section (H), usually will comprise one or more shell-and-tube heat exchangers, wherein the cooling is provided by means of a cooling liquid, most commonly water, with steam driven ejectors to maintain the desired vacuum. The steam required for these vacuum ejectors is indicated as stream (S3) in FIG. 2. However, also any other known technology to condense the off-gasses (17) may be applied here. The resulting condensate (18) is substantially free of ammonia, such that this water flow is an excellent source of water to be used as water feed to the scrubbing unit (D). In the event that the amount of water (18) should be insufficient to meet the required amount of water in this dust scrubber, than additional water (10) can be added. This additional water (10) may originate from the process condensate treatment section (F), however also any other aqueous stream can be used as long as it does not contain any environmental unfriendly volatile components.

It has now been found that the aqueous stream (18) obtained in this way, does not contain ammonia at all, or at any rate in a very low concentration that does not limit the use of the aqueous stream as a source of water for the dust scrubbing section, nor any other environmental unfriendly volatile components. As a result, this stream can be directed directly to the dust scrubbing section, in this way by-passing the process condensate treatment section (F). Some entrained urea may be present in the aqueous stream (18), however this does not harm the dust scrubbing process (D), nor does this urea (present in the liquid form) result in any contamination of the off-gas (8). As a result, the flow (12) feeding the process condensate treatment section, is reduced. As a result, the amount of steam required in this process condensate treatment section reduces as well. For a 'grass-root' urea plant, also the dimensions of the equipment required in the process condensate treatment section can be substantially reduced.

The invention is also well applicable in a 'revamp' or 'debottlenecking' scheme of an existing plant. Processes to revamp or debottleneck urea plants are common in the art. The main objective of such a 'revamp' or 'debottlenecking' of an existing plant usually is the increase of the production capacity of such an existing plant. In those cases where the process condensate treatment section of the existing plant is the limiting factor in obtaining a maximized production, then application of the invention clearly will result in more room available in this process condensate treatment section, thus allowing for an increase of the urea production capacity without applying costly modifications to the equipment in the process condensate treatment section. In those plants where the maximum attainable production capacity is limited by other constraints, then the application of the invention can still be used to further increase the production capacity of the plant, in addition to any other measures to increase the plant capacity by removing or reducing said constraints.

The invention thus also provides a method of modifying an existing urea plant, said plant comprising a synthesis and recovery section (A) which is in fluid communication with an evaporation section (B), said evaporation section being in fluid communication with a finishing section (C) and having a gas flow line to a condensation section (E); said finishing section (C) having a gas flow line to a dust scrubbing section (D); the process comprising the step of adding to the plant an additional evaporation section (G) placed downstream of the dust scrubbing section (D), said additional evaporation section (G) being placed such as to be in fluid communication with the finishing section (C); wherein the additional evaporation section (G) has a gas flow line to an additional condensation section (H), and wherein the additional condensation section (H) is in fluid communication with the dust scrubbing section (D).

In another interesting embodiment, the invention can be used in order to increase the capacity of an existing urea plant. This use comprises the introduction, as described above, of an additional evaporation and condensation loop from and to the dust scrubbing section (D).

The plants as devised or modified according to the invention serve to produce urea. Without necessarily altering the general urea synthesis process, the invention also pertains to a new process for the production of urea, wherein the energy benefits are enjoyed that are associated with using the plant of the invention.

Thus, the invention also pertains to a process for the preparation of urea comprising the steps of (a) one or more synthesis and recovery steps wherein ammonia and carbon dioxide are reacted to form urea and wherein an aqueous solution comprising urea is formed; (b) an evaporation step wherein water is evaporated from the aqueous solution formed in (a) so as to result in a concentrated urea-comprising liquid and an aqueous vapour phase; (c) subjecting the concentrated urea-comprising liquid to a finishing treatment resulting in solid urea, wherein heat is removed by means of a cooling gas such as air; (d) subjecting the cooling gas to dust scrubbing, wherein urea is recovered in an aqueous stream; (e) subjecting said aqueous stream to evaporation so as to result in an additional concentrated urea-comprising liquid and a vapour stream, wherein the evaporation is conducted in an evaporation step separate from the evaporation step (b), wherein the additional concentrated urea-comprising liquid is further subjected to the finishing step (c), and wherein vapours originating from the separate evaporation step are subjected to a separate condensation step (f), and wherein the condensate from said separate condensations step (f) is used in the dust scrubbing step (d).

The invention is not limited to any particular urea production process.

A frequently used process for the preparation of urea according to a stripping process is the carbon dioxide stripping process as for example described in Ullmann's Encyclopedia of Industrial Chemistry, Vol. A27, 1996, pp 333-350. In this process, the synthesis section followed by one or more recovery sections. The synthesis section comprises a reactor, a stripper, a condenser and a scrubber in which the operating pressure is in between 12 and 18 MPa and preferably in between 13 and 16 MPa. In the synthesis section the urea solution leaving the urea reactor is fed to a stripper in which a large amount of non-converted ammonia and carbon dioxide is separated from the aqueous urea solution. Such a stripper can be a shell and tube heat exchanger in which the urea solution is fed to the top part at the tube side and a carbon dioxide feed to the synthesis is added to the bottom part of the stripper. At the shell side, steam is added to heat the solution. The urea solution leaves the heat exchanger at the bottom part, while the vapour phase leaves the stripper at the top part. The vapour leaving said stripper contains ammonia, carbon dioxide and a small amount of water. Said vapour is condensed in a falling film type heat exchanger or a submerged type of condenser that can be a horizontal type or a vertical type. A horizontal type submerged heat exchanger is described in Ullmann's Encyclopedia of Industrial Chemistry, Vol. A27, 1996, pp 333-350. The heat released by the exothermic carbamate condensation reaction in said condenser is usually used to produce steam that is used in a downstream urea processing section for heating and concentrating the urea solution. Since a certain liquid residence time is created in a submerged type condenser, a part of the urea reaction takes already place in said condenser. The formed solution, containing condensed ammonia, carbon dioxide, water and urea together with the non-condensed ammonia, carbon dioxide and inert vapour is sent to the reactor. In the reactor the above mentioned reaction from carbamate to urea approaches the equilibrium. The ammonia to carbon dioxide molar ratio in the urea solution leaving the reactor is generally in between 2.5 and 4 mol/mol. It is also possible that the condenser and the reactor are combined in one piece of equipment. An example of this piece of equipment as described in Ullmann's Encyclopedia of Industrial Chemistry, Vol. A27, 1996, pp 333-350. The formed urea solution leaving the urea reactor is supplied to the stripper and the inert vapour containing non-condensed ammonia and carbon dioxide is sent to a scrubbing section operating at a similar pressure as the reactor. In that scrubbing section the ammonia and carbon dioxide is scrubbed from the inert vapour. The formed carbamate solution from the downstream recovery system is used as absorbent in that scrubbing section. The urea solution leaving the stripper in this synthesis section requires a urea concentration of at least 45% by weight and preferably at least 50% by weight to be treated in one single recovery system downstream the stripper. The recovery section comprises a heater, a liquid/gas separator and a condenser. The pressure in this recovery section is between 200 to 600 kPa. In the heater of the recovery section the bulk of ammonia and carbon dioxide is separated from the urea and water phase by heating the urea solution. Usually steam is used as heating agent. The urea and water phase, contains a small amount of dissolved ammonia and carbon dioxide that leaves the recovery section and is sent to a downstream urea processing section where the urea solution is concentrated by evaporating the water from said solution.

Other processes and plants include those that are based on technology such as the HEC process developed by Urea Casale, the ACES process developed by Toyo Engineering Corporation and the process developed by Snamprogetti. All of these processes, and others, may be used preceding the urea finishing method of the invention.

Urea finishing techniques, such as prilling and granulation, are known to the skilled person. Reference is made to, e.g., Ullmann's Encyclopedia of Industrial Chemistry, 2010, chapter 4.5. on urea.

The invention will hereinafter be further illustrated with reference to the following, non-limiting examples and the figures. The figures are schematic drawings indicating process sections (letters A-G) and streams (numbered). The composition of the streams is clarified in the tables below. The legend for the process sections is as follows: A. Urea synthesis and recirculation section(s); B. Main evaporation section; C. Finishing section; D. Dust scrubbing; E. condensation section; F. Process condensate treatment section; G. Second evaporation section; H. second condensation section.

EXAMPLE 1

A grass root urea plant for the production of 100 ton/h of solid urea is constructed according to the scheme in FIG. 1. The flows in this plant are as indicated in table 1. The feed (12) to the process condensate treatment section is 43130 kg/h. In order to treat this process condensate in the process condensate treatment section F a total of 11708 kg/h (S2) of steam is required.

TABLE 1

| Stream: | phase | UREA kg/h | $NH_3$ kg/h | $CO_2$ kg/h | $H_2O$ kg/h | $N_2$ kg/h | $O_2$ kg/h | TOTAL kg/h | TEMP C. |
|---|---|---|---|---|---|---|---|---|---|
| 1 | gas | | | | 73134 | | | 73134 | 40 |
| 2 | liquid | | 56603 | | | | | 56603 | 25 |
| 3 | liquid | 100211 | 2893 | 1377 | 33262 | | | 137743 | 80 |
| 4 | liquid | 104800 | | | 4367 | | | 109167 | 140 |
| 5 | solid | 99800 | | | 200 | | | 100000 | 50 |
| 6 | gas | | | | | 651950 | 198050 | 850000 | 30 |
| 7 | gas | | 5000 | | 4167 | 651950 | 198050 | 859167 | 95 |
| 8 | gas | | | | 37265 | 651950 | 198050 | 887265 | 45 |
| 9 | liquid | | 5000 | | 7500 | | | 12500 | 45 |
| 10 | liquid | | | | 40598 | | | 40598 | 40 |
| 11 | gas | | 411 | 2893 | 1377 36396 | | | 41077 | 135 |
| 12 | liquid | | 411 | 2893 | 1377 38450 | | | 43130 | 40 |

TABLE 1-continued

| Stream: | phase | UREA kg/h | $NH_3$ kg/h | $CO_2$ kg/h | $H_2O$ kg/h | $N_2$ kg/h | $O_2$ kg/h | TOTAL kg/h | TEMP C. |
|---|---|---|---|---|---|---|---|---|---|
| 13 | liquid | | 3126 | 1678 | 3203 | | | 8007 | 60 |
| 14 | liquid | | | | 46832 | | | 46832 | 40 |
| 15 | liquid | | | | 6233 | | | 6233 | 40 |
| S1 | gas (steam) | | | | 2054 | | | 2054 | 150 |
| S2 | gas (steam) | | | | 11708 | | | 11708 | 150 |

Figure 2:
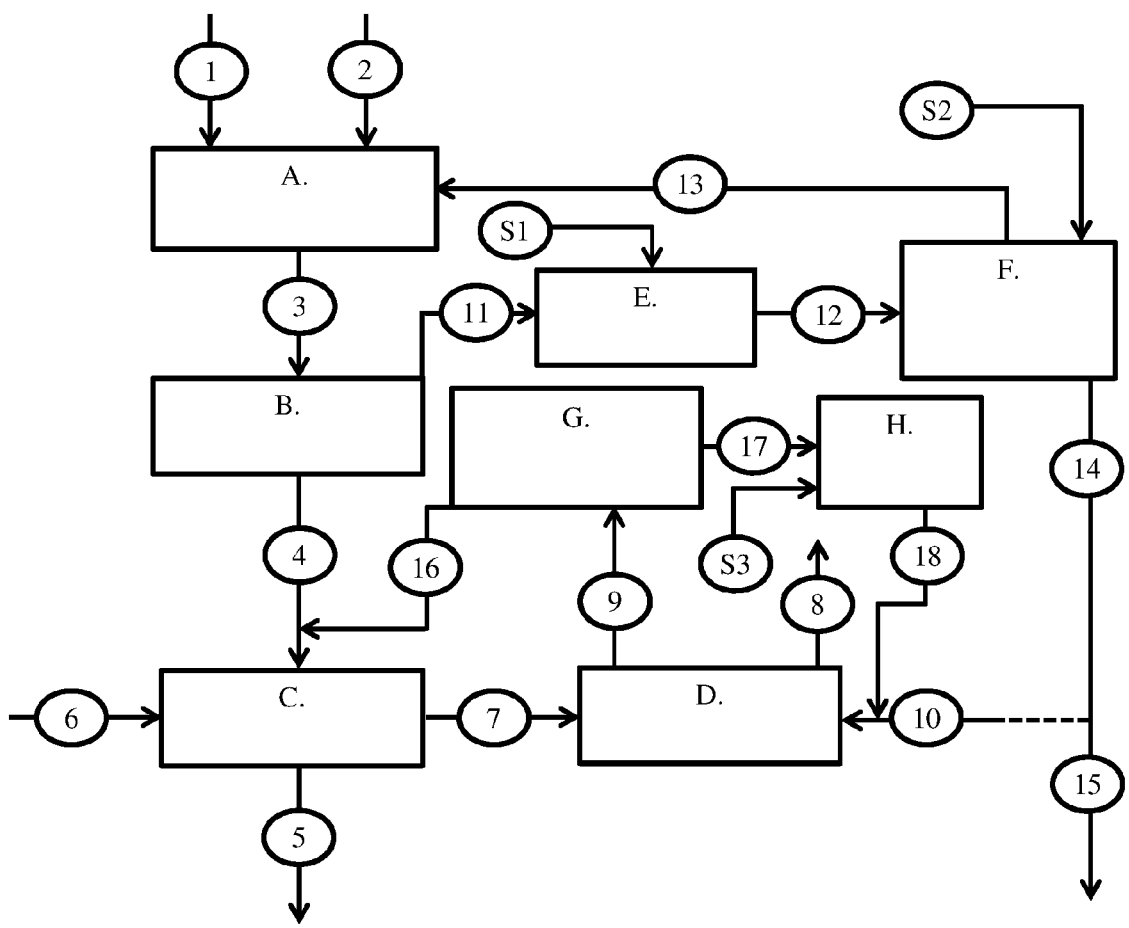
FIG. 2 is a schematic representation of a urea production plant according to an embodiment of the invention.

A grass root urea plant for the same production of 100 ton/h is constructed, using the scheme according to the invention (FIG. 2). The flows in this process are as indicated in table 2. As can be seen from this table, now only 9153 kg/hr (S2) of steam is required in the process condensate treatment section (F).

TABLE 2

| Stream: kg/h | phase | UREA kg/h | $NH_3$ kg/h | $CO_2$ kg/h | $H_2O$ kg/h | $N_2$ kg/h | $O_2$ kg/h | TOTAL kg/h | TEMP C. |
|---|---|---|---|---|---|---|---|---|---|
| 1 | gas | | | 73134 | | | | 73134 | 40 |
| 2 | liquid | | 56603 | | | | | 56603 | 25 |
| 3 | liquid | 100136 | 2889 | 1376 | 33172 | | | 137573 | 80 |
| 4 | liquid | 99800 | | | 4158 | | | 103958 | 140 |
| 5 | solid | 99800 | | | 200 | | | 100000 | 50 |
| 6 | gas | | | | | 651950 | 198050 | 850000 | 30 |
| 7 | gas | 5000 | | | 4167 | 651950 | 198050 | 859167 | 95 |
| 8 | gas | | | | 37265 | 651950 | 198050 | 887265 | 45 |
| 9 | liquid | 5075 | | | 7612 | | | 12687 | 45 |
| 10 | liquid | | | | 32933 | | | 32933 | 40 |
| 11 | gas | 336 | 2889 | 1376 | 29013 | | | 33614 | 135 |
| 12 | liquid | 336 | 2889 | 1376 | 30694 | | | 35295 | 40 |
| 13 | liquid | | 3080 | 1622 | 3134 | | | 7836 | 60 |
| 14 | liquid | | | | 36612 | | | 36612 | 40 |
| 15 | liquid | | | | 3679 | | | 3679 | 40 |
| 16 | liquid | 5000 | | | 208 | | | 5208 | 140 |
| 17 | gas | 75 | | | 7404 | | | 7479 | 135 |
| 18 | liquid | 75 | | | 7778 | | | 7853 | 40 |
| S1 | gas (steam) | | | | 1681 | | | 1681 | 150 |
| S2 | gas (steam) | | | | 9153 | | | 9153 | 150 |
| S3 | gas (steam) | | | | 374 | | | 374 | 150 |

EXAMPLE 2

An existing urea plant, constructed according to the scheme of FIG. 1, is producing 100 ton/h of solid urea. The flows in this plant are as indicated in table 1. In this plant the process condensate treatment section F is the limiting factor in achieving the maximum possible production capacity: in case the production capacity exceeds 100 ton/h, then flow 12 exceeds 43130 kg/hr, which in this plant results in flooding of one of the columns in the process condensate treatment section.

In this plant a (small) second evaporation section (G) and a (small) condensation section (F) are added according to the scheme of the invention (FIG. 2). The flows in the process after this revamp are as indicated in table 3. As can be seen from the table, the plant capacity (5) can be increased to 122 ton/hr, with the same amount of process condensate flow (12) as before (43130 kg/h), such that no flooding of the column in the process condensate treatment occurred at the increased production capacity of the plant. The plant thus was debottlenecked to a production capacity equal to 122% of its original maximum capacity.

TABLE 3

| Stream: | phase | UREA kg/h | $NH_3$ kg/h | $CO_2$ kg/h | $H_2O$ kg/h | $N_2$ kg/h | $O_2$ kg/h | TOTAL kg/h | TEMP C. |
|---|---|---|---|---|---|---|---|---|---|
| 1 | gas | | | 89368 | | | | 89368 | 40 |
| 2 | liquid | | 69167 | | | | | 69167 | 25 |
| 3 | liquid | 122365 | 3530 | 1681 | 40535 | | | 168111 | 80 |
| 4 | liquid | 121954 | | | 5081 | | | 127035 | 140 |
| 5 | solid | 121954 | | | 244 | | | 122198 | 50 |
| 6 | gas | | | | | 796671 | 242014 | 1038685 | 30 |
| 7 | gas | 6110 | | | 5092 | 796671 | 242014 | 1049886 | 95 |

TABLE 3-continued

| Stream: | phase | UREA kg/h | NH$_3$ kg/h | CO$_2$ kg/h | H$_2$O kg/h | N$_2$ kg/h | O$_2$ kg/h | TOTAL kg/h | TEMP C. |
|---|---|---|---|---|---|---|---|---|---|
| 8 | gas | | | | 45537 | 796671 | 242014 | 1084222 | 45 |
| 9 | liquid | 6201 | | | 9302 | | | 15503 | 45 |
| 10 | liquid | | | | 40243 | | | 40243 | 40 |
| 11 | gas | 411 | 3530 | 1681 | 35454 | | | 41076 | 135 |
| 12 | liquid | 411 | 3530 | 1681 | 37508 | | | 43130 | 40 |
| 13 | liquid | | 3763 | 1982 | 3830 | | | 9576 | 60 |
| 14 | liquid | | | | 44739 | | | 44739 | 40 |
| 15 | liquid | | | | 4496 | | | 4496 | 40 |
| 16 | liquid | 6110 | | | 255 | | | 6364 | 140 |
| 17 | gas | | 91 | | 9047 | | | 9139 | 135 |
| 18 | liquid | | 91 | | 9504 | | | 9596 | 40 |
| S1 | gas (steam) | | | | 2054 | | | 2054 | 150 |
| S2 | gas (steam) | | | | 11185 | | | 11185 | 150 |
| S3 | gas (steam) | | | | 457 | | | 457 | 150 |

Note to table 1, 2 and 3: As usual in urea technology, ammonium carbamate in these tables is listed in the form of its constituents (NH$_3$ and CO$_2$). It should be noted that in liquid streams most of the CO$_2$ as listed in the tables actually is present as ammonium carbamate.

The invention claimed is:

1. A process for the preparation of urea comprising:
   (a) one or more synthesis and recovery steps wherein ammonia and carbon dioxide are reacted to form urea and wherein an aqueous solution comprising urea is formed;
   (b) an evaporation step wherein water is evaporated from the aqueous solution formed in (a) so as to result in a first concentrated urea-comprising liquid and an first aqueous vapor phase;
   (c) subjecting said first aqueous vapor phase of (b) to a first condensation step to give an aqueous solution;
   (d) subjecting the first concentrated urea-comprising liquid of (a) to a finishing treatment resulting in solid urea, wherein heat is removed by means of a cooling gas;
   (e) subjecting the cooling gas of (d) to dust scrubbing, wherein urea is recovered in an aqueous stream;
   (f) subjecting said aqueous stream of (e) to evaporation so as to result in a second concentrated urea-comprising liquid and a second vapor phase, wherein the evaporation is conducted in an evaporation step separate from the evaporation step (b), and wherein the second concentrated urea-comprising liquid is recirculated and subjected to the finishing step (d), and
   (g) subjecting the vapor phase originating from the separate evaporation step (f) to a second condensation step separate from the first condensation step (c), and
   (h) using the condensate from said second condensation step (g) in the dust scrubbing step (e).

2. The process of claim 1 wherein the condensate from the second condensation step (g) is subjected to hydrolysis and steam stripping.

3. The process of claim 1 wherein the dust scrubbing of (e) employs circulating urea solution as washing agent and the condensate from the second condensation step (g) is subjected to hydrolysis and steam stripping.

4. The process of claim 3 wherein the aqueous stream of (e) contains 10-60% by weight of urea.

5. The process of claim 4 wherein the condensate from the second condensation step (g) is subjected to hydrolysis and steam stripping.

* * * * *